US 8,178,345 B2

(12) United States Patent
Bennett et al.

(10) Patent No.: US 8,178,345 B2
(45) Date of Patent: May 15, 2012

(54) MULTILAYER CELL CULTURE VESSELS

(75) Inventors: Scott M. Bennett, Limerick, ME (US); Henry J. Cattadoris, Scarborough, ME (US); David A. Kenney, Lunenburg, MA (US); Gregory R. Martin, Acton, ME (US); Allison J. Tanner, Portsmouth, NH (US); Joseph C. Wall, Southborough, MA (US)

(73) Assignee: Corning Incorporated, Corning, NY (US)

( * ) Notice: Subject to any disclaimer, the term of this patent is extended or adjusted under 35 U.S.C. 154(b) by 282 days.

(21) Appl. No.: 12/211,378

(22) Filed: Sep. 16, 2008

(65) Prior Publication Data

US 2009/0298163 A1    Dec. 3, 2009

Related U.S. Application Data

(60) Provisional application No. 61/130,522, filed on May 30, 2008.

(51) Int. Cl.
*C12M 1/24* (2006.01)
*C12M 1/00* (2006.01)
*C12M 1/14* (2006.01)

(52) U.S. Cl. ............... 435/304.2; 435/289.1; 435/299.1; 435/299.2; 435/304.1; 435/304.3

(58) Field of Classification Search ............... 435/340.2, 435/289.1–309.4
See application file for complete search history.

(56) References Cited

U.S. PATENT DOCUMENTS

| 4,042,108 | A | * | 8/1977 | Brethauer | 206/392 |
| 4,770,854 | A | | 9/1988 | Lyman | 422/102 |
| 5,763,267 | A | | 6/1998 | Kurjan et al. | 435/293.1 |
| 2007/0026516 | A1 | | 2/2007 | Martin et al. | 435/297.5 |
| 2008/0003671 | A1 | * | 1/2008 | Martin | 435/304.1 |
| 2008/0206857 | A1 | * | 8/2008 | Kenney et al. | 435/300.1 |

* cited by examiner

*Primary Examiner* — Nathan Bowers
*Assistant Examiner* — Gautam Prakash
(74) *Attorney, Agent, or Firm* — Susan S. Wilks

(57) ABSTRACT

A multilayered cell culture apparatus for the culturing of cells is disclosed. The cell culture apparatus includes a unitary flask body including a rigid upper and lower surface, connected by side walls. The cell growth apparatus comprises multiple cell growth chambers stacked in vertical alignment and orientation within the unitary flask body. The stacked chambers are held in position by unitary connecting columns that run through each cell growth chamber and terminate at the rigid upper and lower surfaces of the apparatus. The cell growth chambers are separated by tracheal spaces that allow air from the external environment to contact the cell growth surface of each individual cell growth chamber.

17 Claims, 2 Drawing Sheets

MULTILAYER CELL CULTURE VESSELS

CLAIMING BENEFIT OF PRIOR FILED U.S. APPLICATION

This application claims the benefit of U.S. Provisional Application Ser. No. 61/130,522, filed on May 30, 2008. The content of this document and the entire disclosure of publications, patents, and patent documents mentioned herein are incorporated by reference.

FIELD OF THE INVENTION

The present invention relates generally to the cellular biological field and, in particular, to a cell cultivating flask.

BACKGROUND OF THE INVENTION

In vitro culturing of cells provides material necessary for research in pharmacology, physiology, and toxicology. The environmental conditions created for cultured cells should resemble as closely as possible the conditions experienced by the cells in vivo. One example of a suitable environment for culturing cells is a common laboratory flask such as demonstrated in U.S. Pat. No. 4,770,854 to Lyman. The cells attach to and grow on the bottom wall of the flask, immersed in a suitable sustaining media. The flask is kept in an incubator to maintain it at the proper temperature and atmosphere.

Gas exchange, particularly the utilization of oxygen by the cells, is a factor that limits the area for cell growth within a cell culture flask. Since flasks for cell culture typically grow attachment dependent cells in a monolayer roughly equal in size to the footprint of the flask, media volume is restricted to an area within the flask permissive to the diffusion of oxygen. Oxygen and carbon dioxide are of particular importance to the culturing of cells. The supply of oxygen for cellular respiration and metabolic function in conventional cell culture containers occupies the head space of the container, e.g., the void space in the container that is above the surface of the cell culture medium. Thus, the volume of the container and the surfaces within conventional cell culture containers are inefficiently used. This results in limiting the rate of gas exchange and/or restricting the equilibration of gases.

The need for large quantities of cells for high throughput screening (HTS) cell based assays continues to motivate organizations to search for methods to achieve larger cell numbers with minimal investment. The challenge is to generate large quantities of cells that all behave the same in cell based assays. In order to provide a solution it is imperative that the cells generated using such methods exhibit similar characteristics such as growth kinetics and response to stimuli. The multilayer flask that is the subject of commonly assigned patent application US 20070026516, incorporated in its entirety herein by reference, describes using several successive layers of cell growth chambers within a unitary vessel, each individual chamber having a gas permeable film and separated from the next by a tracheal space to provide gas exchange between the cells and culture medium and the atmospheric environment surrounding it. This allows for an expansive cell growth surface area when compared to standard traditional flasks such as the industry standard T175 flask. The HYPERFLASK (Corning Incorporated, Corning, N.Y.) vessel has roughly the same dimensions of the industry standard T175 flask (a flask body of approximately 157 mm×122 mm×53 mm) but was developed to generate approximately 10 times as many cells due to the 10 cell growth chambers housed within the flask body. A single HYPERFLASK vessel can be used to seed as many as 100 384 well microplates.

In a commercial embodiment of the HYPERFLASK product, each of the layers or individual cell growth chambers are held together by welds around the perimeter of the flask and press fit to each other in the center such as to form two press fit columns. Under certain conditions of use, pressure can build such that the press fit features cannot hold, and the columns separate leading to potential leaks in the vessel.

SUMMARY OF THE INVENTION

According to an illustrative embodiment of the present invention, a cell growth apparatus for efficient culturing of cells is disclosed. The apparatus includes a unitary flask body including a rigid upper and lower surface, connected by side walls. In one embodiment, the cell growth apparatus comprises multiple cell growth chambers stacked in vertical alignment and orientation within the unitary flask body. The stacked chambers are held in position by unitary connecting columns that run through each cell growth chamber and terminate at the rigid upper and lower surfaces. In one embodiment, the cell growth chambers are separated by tracheal spaces that allow air from the external environment to contact a growth surface of each cell growth chamber.

In another embodiment, a first cell culture chamber is formed by a first top surface, an opposing first bottom surface spaced apart from the first top surface, and a first sidewall around the first chamber and extending between the first top surface and the first bottom surface. A second cell culture chamber is formed by a second top surface, an opposing second bottom surface spaced apart from the second top surface, and a second sidewall around the second chamber and extending between the second top surface and the second bottom surface. The cell culture chambers are held together by at least one unitary connecting column running continuously through the surfaces orthogonal to a plane created by the surfaces.

In yet another embodiment, the first and second chambers are disposed in a stacked arrangement such that the first and second sidewalls are substantially aligned and the first bottom surface is proximate the second top surface, and the first bottom surface and second top surface are spaced apart to form a tracheal space that is in fluid communication with the external environment thereby allowing free gas exchange through the gas permeable, liquid impermeable cell growth bottom surface of each cell growth chamber.

In one embodiment, the lower surface of the cell growth apparatus is a rigid planar piece that is spaced away from the second bottom surface but contacting the second sidewall along a periphery and wherein the cell culture chambers are combined into the integral flask unit.

In another embodiment, the apparatus further contains internal bosses defined by walls connecting each respective top and bottom surface whereby the walls having an inner and outer surface. In one embodiment, the bosses take the form of truncated cones, the diameter at the top of which is larger than the diameter at the bottom. Further, the bosses may contain a top and bottom portion and a step feature on the outer wall of the boss proximate to the bottom portion for fittingly engaging the inner wall of the top portion of a boss from a cell growth chamber immediately below, in such a way that when the bosses are fittingly engaged, the inner walls of the bosses define a cavity through the cell growth chambers. This cavity can be filled with the connecting column to hold all cell growth chambers together. Optionally, the connecting column further comprises a flattened head portion and an elongated pin portion, the flattened head portion engages the rigid lower surface which the terminal end of the pin portion can be melted and fixedly joined to an upper surface of the flask body. In another embodiment, there are a plurality of additional cell growth chambers stacked in succession above the first and second cell growth chambers, each additional cell culture chamber having a top surface, an opposing bottom surface spaced apart from the first top surface, and a sidewall around the chamber and extending between the top surface and the bottom surface, and wherein the connecting column further extends through the surfaces of each additional cell culture chamber thereby connecting the first, second and each additional cell culture chamber. In one embodiment, the dimensions of the flask are substantially identical to that of the industry standard T175 flask.

BRIEF DESCRIPTION OF THE DRAWINGS

The invention is best understood from the following detailed description when read with the accompanying figures. It is emphasized that the various features are not necessarily drawn to scale. In fact, the dimensions may be arbitrarily increased or decreased for clarity of discussion.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1:
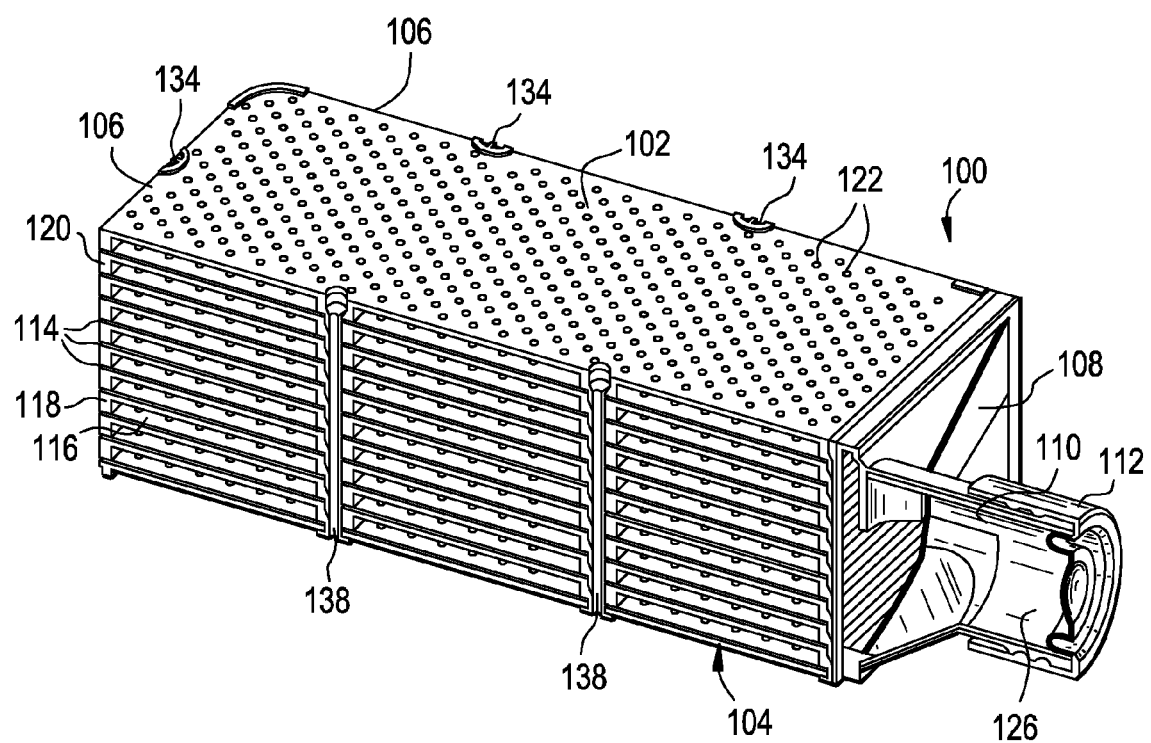
FIG. 1 is a perspective view of an illustrative embodiment of the cell growth apparatus of the present invention in cross section. The section line runs along the bi-symmetrical central axis of the apparatus.
Figure 2:
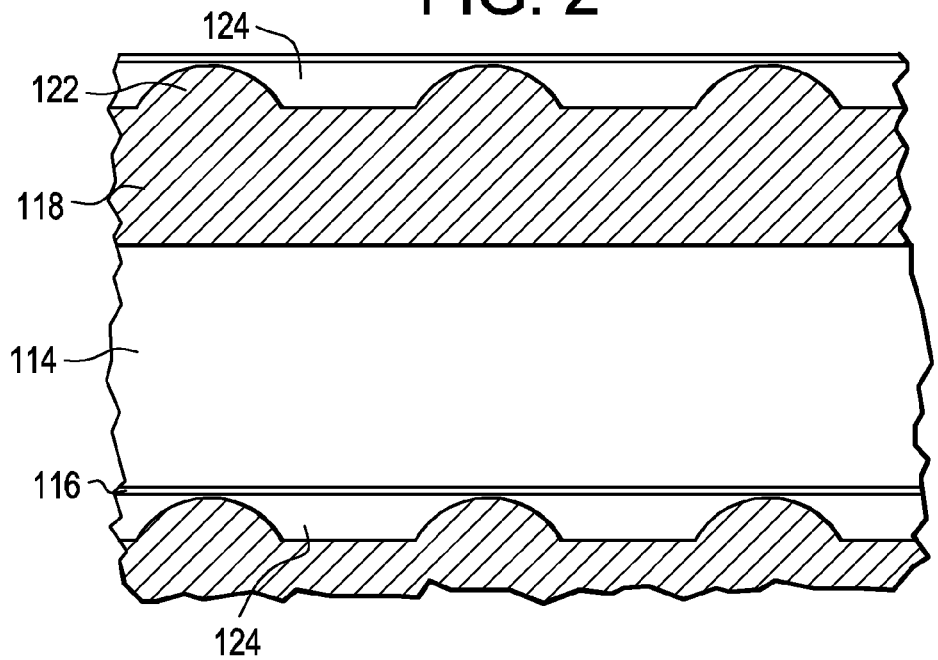
FIG. 2 is a cross-sectional partial view of the cell growth apparatus of FIG. 1 illustrating an individual cell growth chamber.

In accordance with one embodiment of the present invention, a perspective view in cross section of a cell growth apparatus is shown in FIG. 1. The cell growth apparatus 100 of this embodiment takes the form of a flask 100; the flask 100 comprises a rigid upper surface 102 and rigid lower surface 104 surrounded by sidewalls 106, a manifold 108, a threaded neck 110 and a cap 112. In one embodiment, a plurality of individual cell growth chambers 114 are disposed within the internal volume of the flask. The individual cell growth chambers 114 are each defined by a generally transparent bottom surface 116 and a generally transparent top surface 118. The surfaces 116 and 118 are attached to the flask body along the sidewalls 106. In one embodiment, the bottom surfaces 116 within each chamber 114 are made from gas permeable, liquid impermeable material that is capable of supporting cell growth. In one embodiment, each top surface 118 is a rigid, generally gas impermeable material (preferably transparent) that will provide support to the cell growth chamber 114. The top surface 118 includes descending end walls that contact and seal with the bottom surface 116 along their periphery. On the uppermost surface of the top surface 118, spacers 122 in the form of half spherical beads provide structural support for the bottom surface of the cell culture chamber immediately above. As shown in a partial cross sectional view of FIG. 2, tracheal spaces 124, are created between each cell growth chamber 114 by stand-offs descending from the sidewalls of each cell growth chamber. The opposing top surface 118 of each chamber 114 defines a top surface of a cell growth chamber 114 as well as a bottom portion of a tracheal space 124. Each cell growth chamber 114 therefore alternates with a tracheal space 124 in vertical successive orientation. Although the cell growth chamber may have any sized head space or height, in one embodiment, the height of the individual cell growth chambers is between 0.1 and 0.2 inches. Side portals created between the stand-offs in the side wall of the cell growth apparatus allow air to circulate through the tracheal chambers 124 for gas exchange with the external environment via the gas permeable bottom surfaces 116. Accessibility to the cellular growth chambers 114 is achieved via an aperture 126 within the flask body. The aperture 126 has a neck 110 and is connected to the cell growth chambers 114 via the manifold 108.

In one embodiment of the present invention, the chambers 114 permit cellular growth on gas permeable membranes 116 such that multiple cell growth chambers 114 are integral with the body of the apparatus 100 and are capable of being completely filled with nutrient media for the growth of cells. The series of tracheal spaces 124 through the apparatus 100 provide gaseous communication between the cells located within each cell growth chamber 114 and the external environment. The tracheal spaces 124 allow oxygenation of media located within cell growth chambers 114 through the gas permeable bottom surfaces 116. Further, the tracheal spaces 124 may take the form of any air gap or space that will not allow entrance of liquid. The tracheal spaces are formed by multiple spaced stand-offs descending from the sidewalls of each individual cell growth chamber, the height of which will create spacing for air exchange. As a result, a rigid cell culture apparatus 100 having multiple growth chambers 114, alternating with tracheal spaces 124, is constructed to afford the benefit of equivalent gaseous distribution to a large volume of cells. The aperture 126 of the flask is sealable by way of a septum and/or cap 112 to prevent contents of the flask from spilling. Typical height for the tracheal space is between 0.1-0.3 inches.

In one method of constructing the device, each individual cell growth chamber 114 is separately made. A unitarily molded piece incorporating a top surface 118, side walls 120, spacers 122, and circular bosses 128 in the form of descending truncated cones are made. The circular bosses 128 descend from the top surface a distance roughly equivalent with height of the side walls 120. In one embodiment, the circular bosses 122 have a diameter at the top that is larger than the diameter at the bottom. A membrane film making up the bottom surface 116 is heat sealed to the periphery of the cell chamber along the bottom edge of the side walls and is also fused to the circular bottom of each boss 128.

Figure 3:
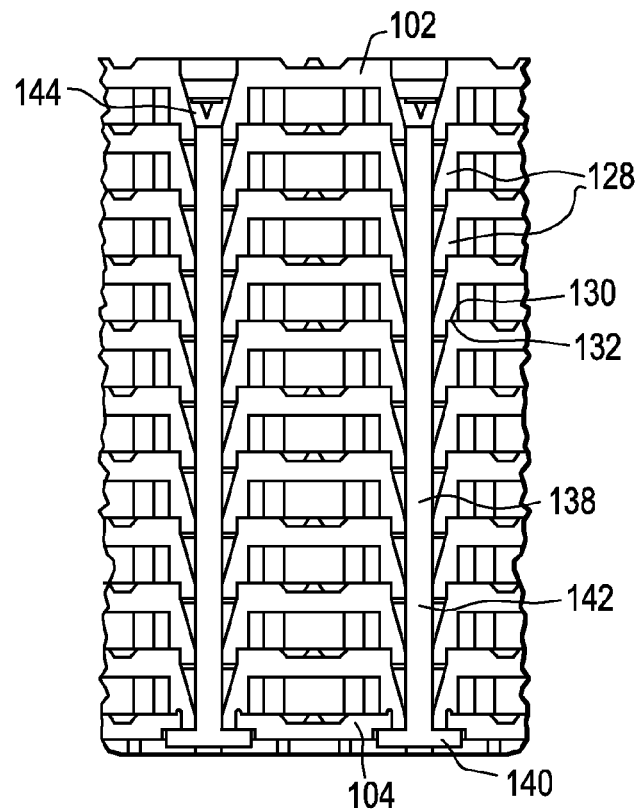
FIG. 3 is a partial and compressed cross sectional view of the cell growth apparatus of FIG. 1.

In one embodiment, the walls defining the circular bosses 128 extend below the level of the height of the side walls 120. As part of this extension, a stepped locking feature 130 embedded within the wall of the boss exists that is capable of mating with the respective top portion 132 of a circular boss from another unitarily molded piece. In this embodiment, the film making up the bottom growth surface 116 is heat welded around the walls of each boss 128 creating a liquid tight seal and leaving holes through the cell growth chamber defined by the walls of the respective bosses 128. Consecutive cell growth chambers may then be snap fitted together by engaging the circular bosses from the respective chambers as shown in FIG. 3.

Once the desired number of cell growth chambers 114 are assembled and locked together through the circular bosses 128, the respective layers are heat welded together along grooves 134 in the outer surface of the flask. A hot metal column is pressed against the outside of the assembled cell growth chambers orthogonal to the plane defined by the cell growth layers and in various groove locations 134 around the periphery of the flask. This has the effect of "heat staking" or melting the polymer in the areas falling into contact with the heated column and thereby welding the assembly together. Although any number of outer welds may be employed, in one embodiment, there are two welds along each respective side wall of the flask.

Under certain conditions of use, the press fit locking features of the bosses in combination with the welds along the outer walls of the flask are not enough to hold the flask unit together and leaking may occur as pressure builds within the flask. In order to provide an additional means of securing the stacked cell growth chambers together, a unitary connecting column 138 may be employed. The connecting column is driven through the cavity created by the consecutively stacked interlocking bosses 128. It extends from the lower surface 104 of the flask 100, through the holes left in each cell growth chamber, to the upper surface 102 of the flask. The connecting column is sealed on both ends to ensure the respective cell growth chambers do not separate, even under pressurized conditions. In one embodiment, the connecting column 138 is made from the same polymer material as the top surface of the flask and has a flattened head portion 140 and an elongated pin portion 142. The flattened head portion engages the bottom of the flask while the elongated pin portion extends through the cell growth chambers and extends beyond the upper surface 102 of the flask 100. Once in position, the end of the connecting column 138 may be heat staked to the upper surface of the flask. As such, the melted tip 144 is mushroomed over and integrally joined with the material comprising the upper surface of the flask. FIG. 3 shows one connecting column (on the right) extending through the flask and above the upper surface created in the boss. It also shows a second connecting column (on the left) having its tip 144 melted along the walls of the boss. The melted tips in combination with the flattened head create a bonded seal holding the stacked cell growth chambers together.

Alternatively, the connecting column may be threaded on the end opposite the headed end such that it can be bolted at the upper surface. In another embodiment, opposing headed pins, one entering the cavity from the lower surface of the flask and the other entering from the upper surface of the flask may be snap fitted together within the cavity creating the unitary connecting column.

The advantage of utilizing the connecting columns has been demonstrated by pressure testing of polystyrene vessels made both with the connecting column and without the connecting columns. In those vessels made without the connecting columns, pressurization testing indicated that failure of the device occurs anywhere between 0.9 and 1.1 psi. For those vessels employing the connecting columns, pressure testing was employed to levels as high 3.0 psi and no failure occurred.

The apparatus 100 of the present invention may be made by any number of acceptable manufacturing methods well known to those of skill in the art. In a preferred method, the apparatus 100 is assembled from a collection of separately injection molded parts. Though any polymer suitable for molding and commonly utilized in the manufacture of laboratory ware may be used, polystyrene is used in one embodiment. Although not required, for optical clarity, it is advantageous to maintain a thickness of no greater than 2 mm.

The top surfaces 118 of each cell growth chamber 114 as well as the manifold 108 and neck portion 110 are injection molded. The bottom surfaces 116 are made from membrane that has been extruded, for example.

Gas permeable, liquid impermeable bottom surfaces 116 may be comprised of one or more membranes known in the art. Suitable materials for use as membranes include for example: polystyrene, polyethylene, polycarbonate, polyolefin, ethylene vinyl acetate, polypropylene, polysulfone, polytetrafluoroethylene (PTFE) or compatible fluoropolymer, a silicone rubber or copolymer, poly(styrene-butadiene-styrene) or combinations of these materials. The membrane may be of any thickness, preferably between about 25 and 250 microns, but ideally between approximately 25 and 125 microns. The membrane allows for the free exchange of gases between the interior of the flask and the external environment and may take any size or shape, so long as the membrane is supportive of cellular growth.

The connecting column 138 may be made from any suitable polymer resin material including polystyrene or any of those deemed suitable by one of skill in the art. Alternatively, the connecting column may be created from an inorganic material such as a metal, glass, ceramic, or glass ceramic.

The gas permeable membrane bottom surfaces 116 are properly affixed to the side walls of the respective top surfaces 118 by any number of methods including but not limited to adhesive or solvent bonding, heat sealing or welding, compression, ultrasonic welding, laser welding and/or any other method commonly used for generating seals between parts. Laser welding around the circumference of the membrane is preferred to establish a hermetic seal around the membrane region such that the membrane is flush with and fused to the face of the side walls such it becomes an integral portion of the interior surface of the apparatus. The parts are held together and are adhesive bonded along the seam, ultrasonically welded, or laser welded. Preferably, laser welding equipment is utilized in a partially or fully automated assembly system.

In order to enhance cell-attachment and growth, the surfaces internal to the apparatus may be treated to enable cell growth. Treatment may be accomplished by any number of methods known in the art which include plasma discharge, corona discharge, gas plasma discharge, ion bombardment, ionizing radiation, and high intensity UV light.

When a cap 112 is provided, it may be a screw cap, snap-fit cap, cap with septum, cap with air holes, or any cap known in the art. In one embodiment, a cap 112 is utilized in which a septum is integral with the cap 112. This will allow a cannula, tip or needle to access the contents of the apparatus without the need for unscrewing. The septum is leak proof, puncturable and capable of resealing once the needle, tip or cannula is removed from the apparatus, even after multiple punctures.

In use, the apparatus of the current invention is employed according to accepted cell growth methods. Cells are introduced to the apparatus 100 though the aperture via the neck (or through a septum in the aperture). Along with the cells, media is introduced such that the cells are immersed in the media. The apparatus is arranged such that the cell containing media covers the cell growth bottom surfaces 116. The apparatus 100 is capable of being completely filled with media since the gas permeable membrane bottom surfaces 116 in combination with the tracheal spaces 124 provide uniform gas distribution to the cell growth bottom surfaces 116. This will further ensure the flow and exchange of gases between flask interior and the external environment. The apparatus is then placed within an incubator and may be stacked together with similar vessels such that a number of cell cultures are simultaneously grown. The apparatus is situated such that the lower surface 104 assumes a horizontal position.

Cell growth is monitored from time to time by microscopic inspection through the generally transparent interior and exterior surfaces of the apparatus 100. Easier accessibility and greater visibility of cellular growth can be achieved when optical lenses having varying magnifications are employed around the outside of the apparatus. During the cell growth process, it may become necessary to extract the exhausted media and insert fresh media. As previously described, media replacement may be achieved through insertion of a canula, for example, through the septum. Alternatively, the media may be replaced by removing the cap 112, in embodiments that offer this option. Once the cells are ready for harvesting, a chemical additive such as trypsin is added to the apparatus through the septum. The trypsin has the effect of releasing the cells from the surfaces of the apparatus. The cells can then be harvested from the flask. The disclosed embodiments of the present invention may be modified to take the shape of any multilayered device, container, apparatus, vessel, or flask currently used in industry. Specifically, multiple layered cylindrical or alternative vessels may utilize gas permeable substrates (internal to the vessel) in combination with tracheal chambers or spaces to provide an improved culturing environment for the growth of cells. Additionally it may be conceived that any multiple layered stacked laboratory device may employ the connecting columns disclosed herein.

Various embodiments of the invention have been described herein. The descriptions are intended to be illustrative, not limiting. Thus, it will be apparent to those skilled in the art that modifications may be made to the invention as described without departing from the scope of the claims set out below.

The invention claimed is:

1. A cell culture apparatus having a plurality of stacked cell culture chambers, comprising:
    at least a first cell culture chamber formed by a first top surface, an opposing first bottom surface spaced apart from the first top surface, and a first sidewall around the first chamber and extending between the first top surface and the first bottom surface; and;
    at least a second cell culture chamber formed by a second top surface, an opposing second bottom surface spaced apart from the second top surface, and a second sidewall around the second chamber and extending between the second top surface and the second bottom surface;
    wherein each of the plurality of cell culture chambers comprise at least one internal boss defined by walls connecting the top and bottom surfaces of each of the plurality of cell culture chambers, wherein the internal boss walls have an inner and outer surface, and each internal boss has a diameter at the top surface of each of the plurality of cell culture chambers that is larger than a diameter at the bottom surface of each of the plurality of cell culture chambers, and
    wherein the internal boss of a first stacked cell culture chamber fittingly engages with the internal boss of a second stacked cell culture chamber with the inner walls of the internal bosses defining a cavity through the plurality of cell culture chambers; and,
    at least one unitary connecting column running continuously through the cavity from a bottom of the cell culture apparatus to a top of the cell culture apparatus.

2. The apparatus according to claim 1, space between the first bottom surface and second top surface.

3. The apparatus according to claim 2, further comprising a rigid planar lower surface spaced away from the second bottom surface but contacting the second sidewall along a periphery and wherein the cell culture chambers are combined into an integral flask unit.

4. The apparatus according to claim 3, wherein the integral flask unit has a substantially rectangular footprint and a substantially uniform height.

5. The apparatus according to claim 4, wherein the tracheal space is an air chamber in communication with the external environment.

6. The apparatus of claim 2, further comprising additional cell culture chambers stacked in succession above the first and second cell culture chambers, each cell culture chamber having a tracheal space formed between the bottom surface of a cell culture chamber and the top surface of an adjacent cell culture chamber.

7. The apparatus according to claim 2, wherein a neck is located within the substantially rectangular footprint and does not exceed the height of the integral flask unit.

8. The apparatus of claim 1, wherein the bosses take the form of truncated cones.

9. The apparatus of claim 1, wherein each internal boss further comprises a top portion and a bottom portion and a step feature on the outer wall of the internal boss proximate to the bottom portion for fittingly engaging the inner wall of the top portion of the internal boss from a cell culture chamber immediately below.

10. The apparatus of claim 1, wherein the unitary connecting column further comprises a flattened head portion and an elongated pin portion, the flattened head portion engaging the bottom of the cell culture apparatus.

11. The apparatus of claim 1, wherein the unitary connecting column is made from a polymer, a glass, a glass ceramic or a metallic material.

12. The apparatus of claim 1, wherein at least one of the bottom surfaces is permeable and liquid impermeable.

13. The apparatus according to claim 1, wherein the internal bosses support a film that forms the top surface or the bottom surface of the cell culture chamber, and the unitary connecting column is separated from the film by the internal boss walls.

14. The apparatus according to claim 13, wherein the unitary connecting column does not support the film.

15. A multilayered flask comprising:
    at least a first cell culture chamber formed by a first top surface, an opposing first bottom surface spaced apart from the first top surface, and a first sidewall around the first chamber and extending between the first top surface and the first bottom surface; and;
    at least a second cell culture chamber formed by a second top surface, an opposing second bottom surface spaced apart from the second top surface, and a second sidewall around the second chamber and extending between the second top surface and the second bottom surface;
    wherein the first cell culture chamber and the second cell culture chamber are stacked in successive orientation to form a multilayered flask having at least two cell culture chambers;
    a plurality of internal bosses defined by walls connecting the bottom surface of the first cell culture chamber with the top surface of the adjacent second cell culture chamber, the internal boss walls having an inner and outer surface, a top surface and a bottom surface, each internal boss having a diameter at each top surface that is larger than a diameter at each bottom surface;

wherein a first internal boss fittingly engages with a second internal boss to formed stacked internal bosses, the inner walls of the stacked internal bosses defining a cavity through the stacked cell culture chambers; and at least one unitary connecting column running continuously through the cavity formed by the stacked internal bosses, from the first top surface to the second bottom surface.

16. The apparatus of claim 15, wherein the connecting column further comprises a flattened head portion and an elongated pin portion, the flattened head portion engaging the second bottom surface.

17. The apparatus of claim 15, wherein the connecting pin is made from a polymer, a glass, a glass ceramic or a metallic material.

\* \* \* \* \*